(12) United States Patent
McCaffrey et al.

(10) Patent No.: US 7,857,804 B2
(45) Date of Patent: Dec. 28, 2010

(54) USE OF BCL INHIBITORS FOR THE PREVENTION OF FIBROPROLIFERATIVE RECLOSURE OF DILATED BLOOD VESSELS AND OTHER IATROGENIC FIBROPROLIFERATIVE DISORDERS

(76) Inventors: Timothy A McCaffrey, 2406 Hildarose Dr., Silver Spring, MD (US) 20902; Zhaoqing Yang, 1309 N. Pierce St., Apartment 104, Arlington, VA (US) 22209; Dmitry Gagarin, 6400 N. Centennial Pl., Apartment D, Glen Burnie, MD (US) 21061

( * ) Notice: Subject to any disclaimer, the term of this patent is extended or adjusted under 35 U.S.C. 154(b) by 445 days.

(21) Appl. No.: 11/848,459

(22) Filed: Aug. 31, 2007

(65) Prior Publication Data

US 2008/0057098 A1   Mar. 6, 2008

Related U.S. Application Data

(60) Provisional application No. 60/841,480, filed on Sep. 1, 2006.

(51) Int. Cl.
*A61M 31/00* (2006.01)
(52) U.S. Cl. ....................... 604/509; 424/423
(58) Field of Classification Search ........................ None
See application file for complete search history.

(56) References Cited

U.S. PATENT DOCUMENTS

| 5,776,905 | A  | 7/1998  | Gibbons   |
| 2002/0137732 | A1 | 9/2002  | Wang      |
| 2003/0199489 | A1 | 10/2003 | Wang      |
| 2005/0239873 | A1 | 10/2005 | Hockenbery |
| 2006/0111288 | A1 | 5/2006  | Cotter    |
| 2006/0178435 | A1 | 8/2006  | Wang      |
| 2006/0241067 | A1 | 10/2006 | Varner    |
| 2006/0247305 | A1 | 11/2006 | Wang      |
| 2006/0247318 | A1 | 11/2006 | Song      |

FOREIGN PATENT DOCUMENTS

WO    WO02097053    12/2002

*Primary Examiner*—Robert A Wax
*Assistant Examiner*—Bethany Barham
(74) *Attorney, Agent, or Firm*—Todd L. Juneau

(57) ABSTRACT

The present invention relates to new use of inhibitors of bcl-2/bcl-Xl family of anti-apoptotic compounds for the treatment of post-angioplasty restenosis and in-stent restenosis. Small molecules of Bcl inhibitors are incorporated into a stent, typically by a fine polymeric coating over the metal, which would be placed during angioplasty of occluded blood vessels, to act on fibroproliferative in-growth. Hollow organs such as urethras, Fallopian tubes and vascular access grafts could be treated in a similar manner to prevent their closure due to fibrosis. Other iatrogenic fibrosis such as adhesions after surgery could also be blocked by this therapy.

10 Claims, 4 Drawing Sheets

USE OF BCL INHIBITORS FOR THE PREVENTION OF FIBROPROLIFERATIVE RECLOSURE OF DILATED BLOOD VESSELS AND OTHER IATROGENIC FIBROPROLIFERATIVE DISORDERS

STATEMENT REGARDING FEDERALLY SPONSORED RESEARCH OR DEVELOPMENT

This invention was made with government support under contract NIH AG12712 awarded by the NIH/National Institutes on Aging. The government has certain rights in the invention.

CROSS REFERENCE TO RELATED APPLICATIONS (Unless Included in the Application Data Sheet)

FIELD OF THE INVENTION

The present invention relates to use of Bcl inhibitors for the prevention of fibroproliferative reclosure of dilated blood vessels and other iatrogenic fibroproliferative disorders. In particular, the present invention relates to the new use of small molecule inhibitors of the Bcl-2/Bcl-XL family of anti-apoptotic proteins for the treatment of post-angioplasty restenosis, in-stent restenosis and the like.

DESCRIPTION OF RELATED ART

The underlying cause of injury-induced fibroproliferative disease is that the reactive repair cells respond to the injury, but fail to undergo apoptosis when the wound is repaired. Thus, they continue to repair the wound, and thus cause excessive matrix production, and inappropriately contract the wound.

Arteries typically become blocked because of progressive atherosclerosis of the vessel. Atherosclerosis is a chronic, low-level inflammatory condition of the arteries which leads to fibroproliferative narrowing of the vessels in some locations. The narrowing of the arteries is especially detrimental when the arteries serve the heart, the brain, and the kidneys. Angioplasty is a highly effective means of dilating occluded coronary, carotid, renal, and peripheral arteries. A catheter with a deflated balloon at the tip is threaded to the site of blockage. The balloon is then inflated which distends the artery, and compresses the blockage. The balloon is then deflated and retracted, leaving an artery with approximately 50% or more of its original diameter. However, in a process called restenosis, the artery will progressively reclose due to elastic recoil, vasospasm, and fibroproliferative regrowth of the artery. The restenosis of coronary arteries occurs in 35-40% treated by balloon angioplasty, and is the major limiting complication. Partially as a function of the high restenosis rate, balloon angioplasty has been substantially with replaced endovascular stents deployed at the time of balloon angioplasty.

To prevent the elastic recoil and the muscular vasospasm that combine to compromise the lumen diameter, a metallic wire mesh stent was devised which could provide a scaffold to keep the artery open. The wire mesh is collapsed around the balloon, threaded into the occlusion, expanded, and the balloon retracted, leaving the expanded wire mesh to hold the artery open. While preventing the vasospasm and elastic recoil of the artery, stents do not prevent the fibroproliferative response to the vascular damage, and 25% to 40% of patients will slowly re-occlude the artery due to in-growth of repair cells through the wire mesh stent.

Thus, the last major element of restenosis that had to be overcome was the fibroproliferative in-growth of cells through the wire mesh stent. This was overcome by Drug eluting stents (DES), which are stents with coatings of suppressive agents. The two major drug eluting stents (DES) are the Cypher stent (Johnson & Johnson, Cordis Division) that is coated with rapamycin, and Taxus, (Boston Scientific) that is coated with taxol, an antimitotic agent. Both of these DES are very effective, reducing the restenosis rate from 25-40% to 5-10%. But both available DES have significant percentages of patients that exhibit resistance to the therapy. The present invention provides a third treatment strategy that is possibly more effective. The present invention describes a different drug class that can achieve possibly better effects.

US2006052369 discloses the use of benzodiazepine derivatives in conjunction with stenosis therapy to treat compromised (e.g., occluded) vessels by using metallic intravascular stents inserted by catheter, in the treatment of a number of conditions associated with the faulty regulation of the processes of programmed cell death, autoimmunity, inflammation, hyper proliferation, vascular abnormalities, and the like.

US20050239873A1 discloses 2-methoxy antimycin derivatives or analogs and the methods for treating apoptosis-associated diseases such as neoplastic disease (e.g., cancer) or other proliferative diseases associated with the over-expression of a Bcl-2 family member protein.

US20020137732A1 discloses promotion of apoptosis in tumor cells using tricyclo-dibenzo-diazocine-dioxides, non-peptide pharmaceuticals, which are cell permeable small molecules that bind to a pocket of Bcl-2 and block the Bcl-2 anti-apoptotic function in cancer cells and tumor tissue exhibiting Bcl-2 protein over expression.

US20060247318 A1 discloses the method of inhibiting Stat3 activity in a cell by contacting the cell with "STA-21" or its derivative, analog, prodrug or pharmaceutically acceptable salt and their use for inducing cell death & sensitizing cells. They inhibit the growth of a cell with elevated Stat3 activity thus inducing apoptosis (hyperproliferative disease) and/or cell cycle arrest in a cell. Any oncolytic agent that is routinely used in a cancer therapy is used in the compositions.

US20060247305 discloses the method of inhibiting anti-apoptotic Bcl-2 family members in a cell by contacting the cell with a compound with the following formulae.

Formulae:

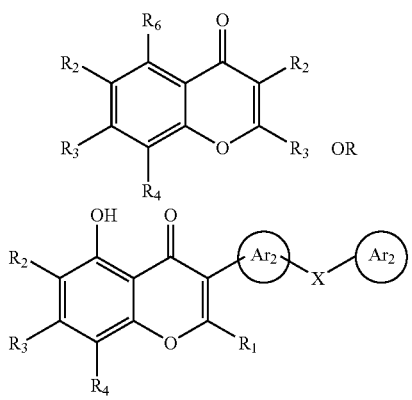

-continued

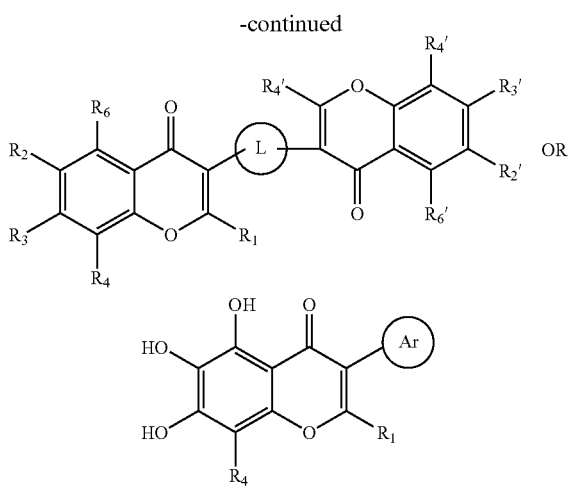

The method of rendering further comprises contacting the cell with an inducer of apoptosis (which is chemotherapeutic agent or radiation). Disorder responsive to the induction of apoptosis is a hyperproliferative disease, viz., cancer. By inhibiting anti-apoptotic Bcl-2 family members, compounds disclosed sensitize cells to the inducers of apoptosis and, in some instances, they themselves induce apoptosis.

US20060241067A1 discloses methods for detecting & inhibiting angiogenesis, cell migration, cell adhesion and/or cell survival in endothelial and non-endothelial cells as well as in normal and tumor cells.

US20060178435A1 discloses the preparation and use of apogossypolone that functions as an inhibitor of Bcl-2 family proteins for inhibiting hyperproliferative cell growth, inducing apoptosis in cells & for sensitizing cells to the induction of apoptotic cell death. Apogossypolone. The present invention includes the method of treating, ameliorating or preventing a disorder responsive to the induction of apoptosis and hyperproliferative disease (cancer) in an animal. This invention also contemplates that the inhibitors of anti-apoptotic Bcl-2 family proteins satisfy an unmet need for the treatment of multiple cancer types, either when administered as monotherapy (by inducing apoptosis) in cancer cells or when administered in a temporal relationship with other cell death-inducing cancer therapeutic drugs or radiation therapies.

US20060111288A1 discloses a method for the treatment of cancer by application of anti-tumor agent HA14-1, which causes intra-mitochondrial generation of reactive oxygen species in tumor cells by a mechanism independent of the peripheral benzodiazepine receptor. This invention also includes a method for inducing apoptosis of cells and for sensitizing cells to anti-neoplastic treatment.

WO02097053 discloses naturally occurring and chemically synthesized small molecules antagonists of Bcl-2 family proteins particularly gossypol derivatives, and their use as antagonists of the anti-apoptotic effects of Bcl-2 and Bcl-XL proteins. A gossypol compound, or an analogue thereof, is administered in conjunction with a tumor cell apoptosis promoting agent (e.g., Geranylgeraniol[3,7,11,15-tetramethyl-2,6,10,14hexadecatraen-1-ol]). The present invention also contemplates that increasing tumor apoptosis reestablishes normal apoptotic control associated with basal levels of Bcl-2 and/or Bcl-XL expression.

US20030199489A1 discloses small molecule antagonists of Bcl-2 family proteins such as Bcl-2 and/or Bcl-XL, in particular, non-peptide cell permeable small molecules (e.g., tricyclo-dibenzo-diazocine-dioxides) that bind to a pocket in Bcl-2/Bcl-XL and block the anti-apoptotic function of these proteins in cancer cells and tumor tissues exhibiting Bcl-2 protein over expression. This patent further discloses that the small molecules of the invention are active at the BH3 binding pocket of Bcl-2 family proteins (e.g., Bcl-2, Bcl-XL, and Mcl-1).

U.S. Pat. No. 5,776,905 discloses, apoptotic regression of neointimal cells due to reduction of Bcl-X levels by treatment of the cells with antisense genes interfering with transcription/translation. The patent further discloses that Bcl-X is elevated in atherosclerotic lesions and claims methods to use the antisense oligonucleotide for the treatment of intimal hyperplasia, restenosis, and atherosclerosis.

SUMMARY OF THE INVENTION

The present invention relates to the new use of small molecule inhibitors of the Bcl-2/Bcl-$X_L$ family of anti-apoptotic compounds for the treatment of post-angioplasty restenosis and in-stent restenosis. The Bcl inhibitory compounds of the present invention are incorporated into a stent, typically in the form of a fine polymeric coating over the metal, which is then placed in the occluded vessels by angioplasty to prevent the fibroproliferative in-growth. The present invention is also used to treat hollow organs such as urethras, Fallopian tubes and vascular access grafts in a similar manner to prevent their closure due to fibrosis. Further, the present invention is also used in the treatment of iatrogenic fibrosis such as adhesions after surgery.

The present invention is based on the discovery that cells which are resistant to apoptosis contribute to the fibroproliferative process. The present invention is further based on the discovery that the Bcl-Xl gene is increased in cells that are resistant to apoptosis, which is also called as programmed cell death. The small molecules of the present invention block the Bcl family members and convert the cells that are resistant to apoptosis into cells that are sensitive to apoptosis. Furthermore, the present invention is based on the discovery that genetic inhibition by expression of short-hairpin RNA (shRNA) that has the effect of causing targeted degradation of the Bcl-Xl mRNA and thus reduced protein synthesis, also cause cells to become more sensitive to apoptosis.

The small molecules of the present invention comprises 2-methoxyantimycin $A_3$ (abbreviated AA3 in the present application is an antimycin analog which binds the hydrophobic groove of Bcl-2 and Bcl-Xl and inhibits their antiapoptotic function); Antimycin A (Chemical composition similar to AA3 above, except containing a mixture of antimycins A1, A2, A3, and A4); 2,9-dimethoxy-11,12-dihydrodibenzo[c,g][1,2]-diazocine 5,6-dioxide (A) and 5,5'-Dimethoxy-2,2'-dinitrosobenzyl (B) Used as a mixture of the tautomers (A) and (B) (abbreviated as BCL in present application); 2,3-DCPE HCl (2,[[3-(2,3-dichlorophenoxy)propyl]amino]ethanol-HCl); Gossypol (2,2'-bis(8-Formyl-1,6,7-trihydroxy-5-isopropyl-3-methylnaphthalene)); HA14-1 (Ethyl-2-amino-6-bromo-4-(1-cyano-2-ethoxy-2-oxoethyl)-4H-chromene-3-carboxylate).

The object of the present invention is to treat post-angioplasty restenosis and in-stent restenosis with the use of small molecule inhibitors of the Bcl-2/Bcl-XL family of anti-apoptotic compounds.

Another object of the present invention is to prevent/treat closure of hollow organs such as urethras, Fallopian tubes, and vascular access grafts that may occur due to fibrosis.

Further, another object of the invention is to treat iatrogenic fibrosis such as adhesions after surgery.

DETAILED DESCRIPTION OF THE INVENTION

Definitions

Figure 1:
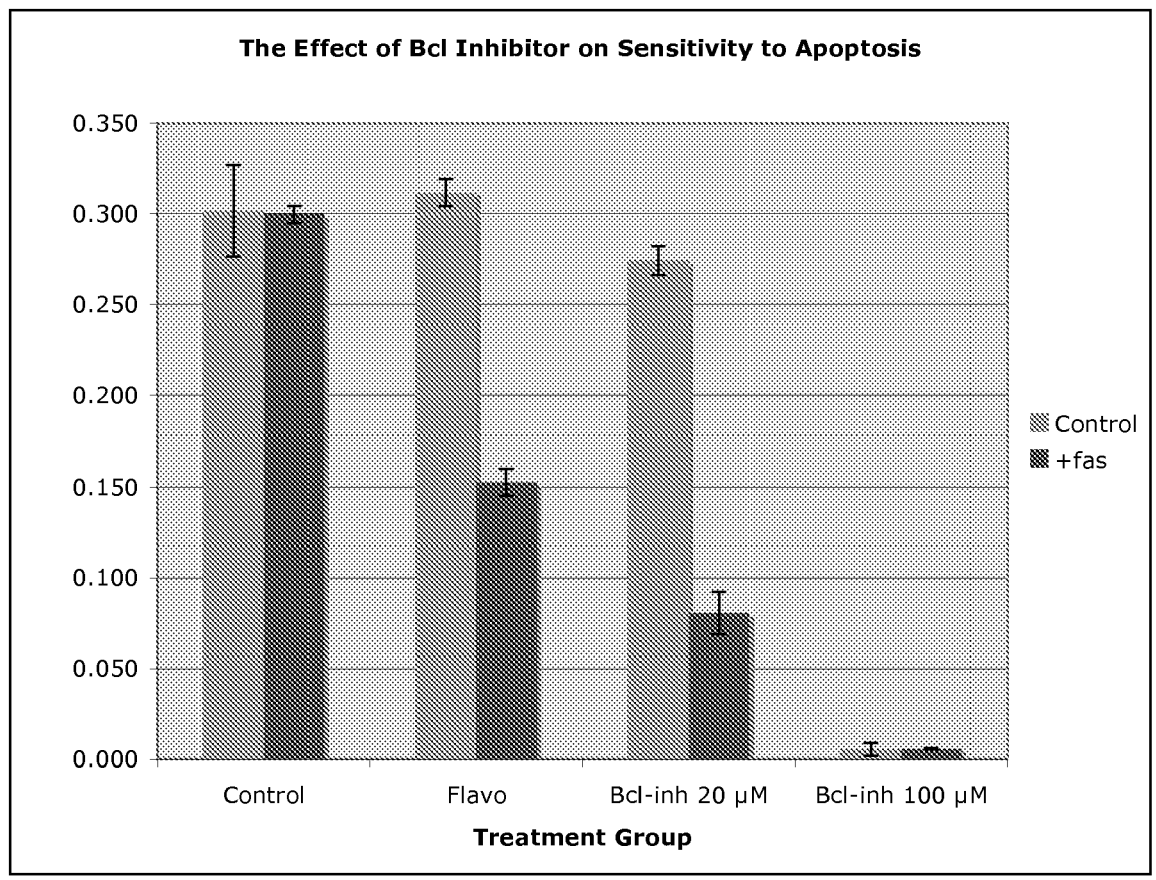
FIG. 1: depicts the effect of Bcl inhibitor on sensitivity to apoptosis

The term "apoptosis" refers to a regulated network of biochemical events which lead to a selective form of cell suicide, and is characterized by readily observable morphological and biochemical phenomena, such as the fragmentation of the deoxyribo-nucleic acid (DNA), condensation of the chromatin, which may or may not be associated with endonuclease activity, chromosome migration, margination in cell nuclei, the formation of apoptotic bodies, mitochondrial swelling, widening of the mitochondrial cristae, opening of the mitochondrial permeability transition pores and/or dissipation of the mitochondrial proton gradient and the like.

The present invention relates to the new use of small molecule inhibitors of the Bcl-2/Bcl-$X_L$ family of anti-apoptotic proteins for the treatment of post-angioplasty restenosis and in-stent restenosis. The Bcl inhibitory compounds of the present invention are incorporated into a stent, typically in the form of a fine polymeric coating over the metal, which is then placed in the occluded vessels by angioplasty to prevent the fibroproliferative in-growth.

Certain preferred compounds and uses are described below. The present invention is not limited to these particular compositions and uses.

As Bcl-X and Bcl-2 are an important part of cell survival in non-atherosclerotic arteries, and in unrelated tissues such as brain, liver, etc., it is envisioned that the drugs would be used locally at the site of angioplasty, or after other physician-initiated (iatrogenic) tissue damage. Local administration into arteries and other hollow organs such as the ureter, can be achieved several ways:

In one embodiment, the drugs are delivered into the artery wall directly. According to this embodiment the drug is delivered through balloon catheters. The balloon catheters are fabricated with semi-permeable membranes that allow direct installation of a drug into the artery wall at the time of angioplasty. In this embodiment, the small molecule drug may be conjugated to a higher molecular mass protein or polymer that slows its diffusion from the angioplasty site, and thereby prolongs its action. Examples of conjugating agents include, but are not limited to: collagen, elastin, polyvinyl alcohol (PVA), dextran, cellulose, proteoglycans, polyethylene glycol (PEG), and other large, non-immunogenic polymers.

In other embodiments, the catheters have been fabricated iontophoretically (electrically) to instill drug into the artery wall. As explained in the above embodiment, the drug is likely conjugated to a polymer to slow its diffusion. In this case, charged molecules are advantageous.

In some other embodiments, other catheters have been devised in which the balloon is not permeable, but is coated with a polymeric layer that transfers to the artery wall upon application of physical contact and pressure. Likewise, the drug may be conjugated to a polymeric substance to slow down the diffusion as explained in the above embodiments.

According to another embodiment, the drugs are coated onto a metallic or polymeric stent. Stents are typically wire-mesh tubes, which physically dilate the artery and prevent elastic recoil and vasospasm in the artery.

In one embodiment, the drug can be itself polymerized by linker/adapter groups and covalently attached to the stent. The drug is liberated when it contacts the vessel by virtue of enzymatic (esterase, proteinase, etc) or non-enzymatic chain breakage (free radicals). In some embodiments, the drug is admixed with a polymeric coating that is applied to the stent prior to insertion, expansion, and deployment.

The types of polymers which can be used is extensive, and includes, but is not limited to: polyvinyl alcohol (PVA), polytetrafluoroethylene (PTFE), Teflon, phosphorylcholine, cationically modified phosphorylcholine polymer, poly (vinyl alcohol)-graft-poly(lactide-co-glycolide), polyethylene terephthlate, aliphatic polyester, acrylate-based polymers, carbon nanoparticles, collagen, 2-chloroparacyclophan, poly (2-chloroparaxylylene) layer modified by treatment with a sulfur dioxide plasma, polyurethane, PTFEP (poly(bis(trifluoroethoxy)phosphazene), polylactide, fluorinated polyphosphazenes and polymethacrylates, Carbofilm, hyaluronan, heparin-polycaprolactone-L-lactide, denatured collagen-polylactic-polyglycolic acid, poly-L-lactic acid, gelatinous photogel, and silicon carbide.

The stent structure can be made of many distensible metallic alloys and metals including, but not limited to: nitinol, titanium, magnesium, tantalum, stainless steel, carbon, chromium, copper, silver, gold, and various alloys of each. Stents made of polymers have also been described and also acceptable for delivery of the present compounds.

According to one embodiment, the principal application for this technology is as a drug, which is applied locally to an occluded artery in the process of angioplasty. The drug slowly elutes from the stent coating and induces sensitivity to apoptosis in reactive repair cells. The drug diffuses for possibly up to 2 weeks, preventing excessive repair of the vessel wall. The specific vessels envisioned include, but are not limited to: coronary arteries, carotid arteries, renal arteries, iliac, femoral and other peripheral arteries, especially in the lower extremities, anastomotic junctions of peripheral veins or internal mammary arteries used in bypass grafting of blocked arteries.

According to another embodiment, a secondary, but potentially large, and important application for the technology are other hollow organs such as ureter, bladder, prostate, urethra, Fallopian tubes, and other hollow organs. Ureteric stents have been reported, such as caprolactone-coated self-reinforced self-expandable poly-L-lactic acid bioabsorbable urethral stents.

Surgical adhesions occur by a similar fibroproliferative process. According to one embodiment, by minor changes to the manufacturing process, the drug is incorporated into a thin polymeric film, which is inserted between organs or tissues to prevent them from developing a fibroproliferative adhesion. Examples include: inappropriate adhesion of female reproductive organs (i.e. ovary, Fallopian tubes, etc.) with the gastrointestinal tract, or adhesion of the GI tract to the diaphragm.

Further, according to another embodiment, a major application is in the prevention of excessive cutaneous wound repair, which is called hypertrophic scars, or keloids. The drug is applied topically after surgery, or eluted from a polymeric bandage, suture, or coating to prevent excessive scarring in susceptible individuals.

The small molecules of the present invention comprises:

2-methoxyantimycin $A_3$ (Biomol, Plymouth Meeting, Pa.). Molecular formula: $C_{27}H_{38}N_2O_9$ (abbreviated AA3 in the present application). AA3 is an antimycin analog which binds the hydrophobic groove of Bcl-2 and Bcl-Xl and inhibits their antiapoptotic function [1].

Antimycin A (Sigma, A8674, abbrev. AA). Chemical composition similar to AA3 above, except containing a mixture of antimycins A1, A2, A3, and A4.

2,9-dimethoxy-11,12-dihydrodibenzo[c,g][1,2]-diazocine 5,6-dioxide (A) and 5,5'-Dimethoxy-2,2'-dinitrosobenzyl (B). Used as a mixture of the tautomers (A) and (B). (abbreviated as BCLI in present application).

2,3-DCPE HCl (Biomol #AP-306). F.W. 300.6, $C_{11}H_{15}CL_2NO_2$—HCl, 2,[[3-(2,3-dichlorophenoxy)propyl]amino]ethanol-HCl.

Gossypol. (Sigma Cat # G8761, FW 518.55), $C_{30}H_{30}O_8$, 2,2'-bis(8-Formyl-1,6,7-trihydroxy-5-isopropyl-3-methyl-naphthalene).

HA14-1 ($C_{17}H_{17}BrN_2O_5$) F.W. 409.2 (Biomol CM-122) Ethyl-2-amino-6-bromo-4-(1-cyano-2-ethoxy-2-oxoethyl)-4H-chromene-3-carboxylate.

Identification of sensitive and resistant cells: Using cells derived from human atherosclerotic lesions, we identified their apoptotic (programmed cell death) response to a known trigger: fas ligation. According to the above theory, cells which undergo apoptosis in response to fas ligation are 'normal' repair cells which would not cause excessive repair/fibrosis. Conversely, cells which are resistant to fas ligation, are proposed to be 'abnormal' repair cells which would cause excessive wound repair and hence, restenosis after angioplasty and stenting.

Microarray analysis of sensitive and resistant cells: The full mRNA expression pattern of the sensitive and resistant cells was examined by Affymetrix microarrays, and genes which were differentially expressed were identified. These genes were further filtered by preference for genes which might alter sensitivity to apoptosis. A set of genes were identified and further examined by quantitative PCR and Western blot. Likely candidate genes were caspase 1, BAD, cyclin D1, STAT6 and Bcl-Xl. These results are described in [2]. While the expression patterns suggest that these factors are involved, the proof is whether altering their expression has the predicted effect upon the response to fas ligation.

Immortalization/cloning of sensitive/resistant cells: A problem in working with primary cells is that cells which are initially sensitive to apoptosis become resistant to apoptosis after a short time in culture. Thus, it was desirable to stabilize the cells and so some of these repair cells spontaneously immortalized and then individual cells were plated in separate wells and allowed to grow into separate clonal lines. Then, their sensitivity or resistance to fas ligation was determined. Clones that were sensitive and others that were resistant were selected for further study.

Inhibition and over expression of selected apoptosis regulators: Both inhibitors of the candidate gene products, and genetic overexpression of the gene was employed in order to determine whether the gene is actually involved in resistance to apoptosis. Our studies indicated that cyclin D1 inhibitors seem to reverse the resistance to apoptosis [3], though there are prior publications and patents to this effect. A separate manuscript describes the fact that several other genes, while promising targets, did not regulate sensitivity/resistance to apoptosis in these vascular repair cells. The examples include BAD, caspase 1, and STAT6. However, Bcl-Xl (BCL2L1) proved to be a very potent modulator of sensitivity to apoptosis [4]. The evidence for this is three-fold:

1) Genetic over expression of Bcl-Xl in cells sensitive to apoptosis converted them to apoptosis-resistant.

2) Small molecule inhibitors of Bcl-2 and/or Bcl-Xl convert cells that are resistant into cells that are sensitive to apoptosis.

3) Genetic inhibition by expression of short-hairpin RNA (shRNA), which has the effect of causing targeted degradation of the Bcl-Xl mRNA and thus reduced protein synthesis, also caused cells to become more sensitive to apoptosis.

In the present examples, AA was used in concentrations of 5-50 µg/ml in Medium 199 with 1% fetal bovine serum (FBS). BCLI was used in concentrations ranging from 5-100 µM. AA3 was used in concentrations from 10-50 µg/ml. Gossypol was used in concentrations from 0.5-5 µM.

Cells for study were derived from human carotid artery atherosclerotic lesions, by published methods [2]. Additionally, cell lines were subcloned and tested for sensitivity to fas ligation. In the present studies, clonal lines with known resistance to fas ligation were used [2].

Induction of apoptosis was achieved by reduction of serum concentration from 10% to 1% FBS for 24 hours prior to adding an activating antibody to fas (CH11, Upstate Biotechnology) at a typical concentration of 50-500 ng/ml. Typically 24-48 hours after fas ligation by CH11, cell survival was determined by measuring metabolic activity by the MTT method. MTT is converted to blue dye by metabolically active and viable cells, and thus cells that have undergone apoptosis do not metabolize MTT, thereby creating less blue color [2].

EXAMPLE 1

Using the cell line R1, it was observed that pretreatment with BCL-inhibitor (BCLI) at 20 µM had little or no effect upon cell survival in the absence of the activating antibody to fas ligation (CH11, FIG. 1). However, in the presence of fas, the cells pretreated with BCLI underwent a high degree of apoptosis (70% cell death). It is important to reiterate that at this dose (20 µM), BCLI has little or no adverse effect on cell number or metabolism, as demonstrated in the control group which contains the drug, but not a fas ligating agent. Thus, the drug is neither toxic nor capable of inducing apoptosis alone at this concentration.

This compares favorably with a known sensitizing agent, flavopiridol, which has likewise been shown to inhibit restenosis in animal models [5]. At a higher concentration of BCLI (100 µM), there was a substantial effect on cell survival even in the absence of fas ligation. This suggests that at relatively low doses BCLI sensitizes cell to apoptosis induced by fas ligation, while not itself inducing apoptosis. At higher doses, apoptosis is induced by BCLI alone.

Referring to FIG. 1, A human cell line derived from carotid artery atherosclerotic lesion was plated at known density and then subgroups of 3 wells were treated with various drugs prior to exposure to fas ligation by the activating $CH_{11}$ antibody (+fas). Pretreatment with flavopiridol (Flavo, 50 nM) or BCLI (Bcl-inh, 20 µM or 100 µM) was followed 24 hours later by addition of CH11 activating antibody to fas (50 ng/ml). After fas ligation, cell survival was evaluated 24 hours later by measuring the number of viable cells using the metabolic dye MTT, which is converted to a blue dye that absorbs at 570 nm. Values reflect the mean±s.e.m. (n=3 per group).

EXAMPLE 2

In addition to the BCL-inhibitor, this sensitizing effect was also observed with AA. As above, a human atherosclerosis-derived cell line with known resistance to fas ligation was used for study. In this case, the cell line was stably infected with a retrovirus expressing either an irrelevant marker gene (green fluorescent protein, GFP) or the marker gene and Bcl-Xl. In the GFP-only expressing cell line (R1GFP), fas ligation (50 ng/ml CH11) in low serum (1% FBS) led to only 15% cell death (85% survival) (see FIG. 2). However, 24 hour pretreatment with AA3 (20 µg/ml) had only a small effect on cell survival in the absence of fas, but caused marked apoptosis in the presence of fas (70% apoptosis). BCLI (20 µM) had a similar effect, though caused slightly more apoptosis alone. A comparable effect was observed with interferon-gamma (50 U/ml), which is a known sensitizing agent [6]. A MAPkinase inhibitor SP600125 (SP), had a more general inhibitory effect at the selected concentration (20 µM).

In one example, to determine whether the effect of BCLI and AA was via interaction with their intended targets (Bcl-Xl and Bcl-2), the drugs were tested in R1 cells over-expressing Bcl-Xl (R1 bclXL). In these cells, the BCL inhibitors were markedly less effective, presumably because they had to compete with, and inactivate a much larger amount of endogenous Bcl-Xl (see FIG. 2, right bars). Likewise, interferon was less effective, possibly because its effect also depends upon modulating the effect of Bcl-Xl. The SP was still an effective inhibitor, though less potent than in control GFP-expressing cells.

Figure 2:
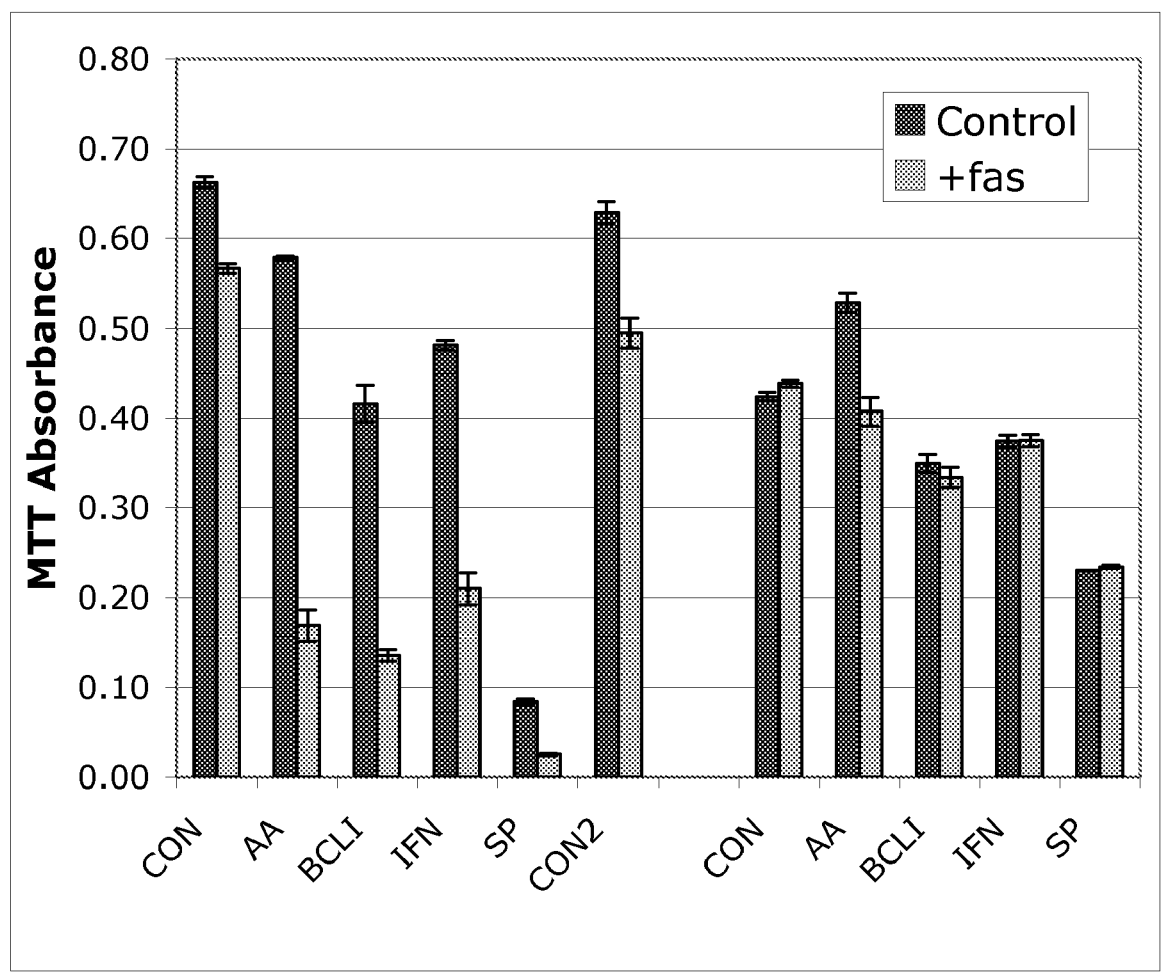
FIG. 2: depicts the effect of AA, BCLI, interferon gamma (IFN) and SP600125 (SP).

Referring to FIG. 2, human atherosclerosis-derived cells were pretreated with the specified drugs for 24 prior to treatment with the activating fas antibody CH11 (50 ng/ml). After the fas treatment, 24 hours later cell survival was measured by MTT wherein dead cells do not generate MTT absorbance. The drugs used were AA (20 µg/ml), BCLI (20 µM), interferon-gamma (IFN, 50 U/ml), and SP600125 (SP, 20 µM). The upper panel reports the MTT optical density (absorbance at 570 nm) without (control) or with fas ligation (+fas) as the mean, with error bars indicating±standard error of measurement (s.e.m., n=3 per group). The lower panel expresses % survival based on the MTT values above (MTT+fas/MTT Control)×100.

EXAMPLE 3

Figure 3:
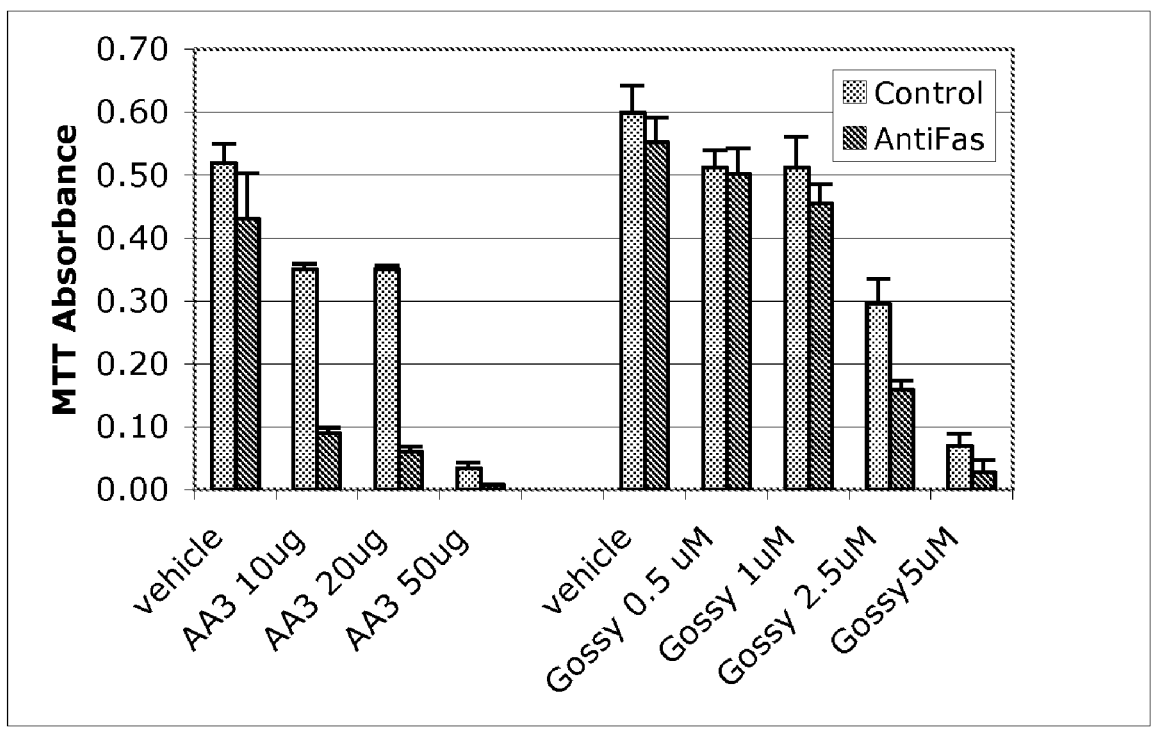
FIG. 3: depicts the effect of 2-Methoxy-antimycin A3(AA3) and Gossypol on the sensitivity to apoptosis in human lesion cells

In a format similar to the procedures above, 2 other potential inhibitors were tested: antimycin A3 and gossypol. Antimycin A3 (2-methoxyantimycin A3) is an analog of antimycin which inhibits Bcl-2 and Bcl-Xl by binding to their hydrophobic groove. AA3, unlike antimycin A, does not cause general mitochondrial toxicity by inhibiting mitochondrial electron transport. Gossypol is a potential male infertility agent that also counteracts the activity of Bcl family members. As shown in FIG. 3, AA3 is effective at increasing sensitivity to apoptosis from 20% to 80% death at both 10 and 20 µg/ml. At higher concentrations, AA3 induced death even in the absence of fas ligation. Gossypol showed a narrow window in which it induced any sensitivity to fas ligation: at 2.5 µM it reduced survival in the presence of fas from 80% to 50%, though it also had a significant fas-independent effect on survival at 2.5-5 µM.

FIG. 3 depicts the effect of 2-methoxy-antimycin A3 (AA3) and gossypol on the sensitivity to apoptosis in human lesion cells. Human lesion cells were plated and treated as above for 24 hours with the specified concentrations of drug. Fas ligation was initiated with 50 ng/ml of activating antibody CH11 and 24 hours later the number of cell surviving was measured by their metabolism of MTT. Bars are mean±s.d. (n=4 per group). A reduction in MTT levels indicates cell death.

EXAMPLE 4

Figure 4:
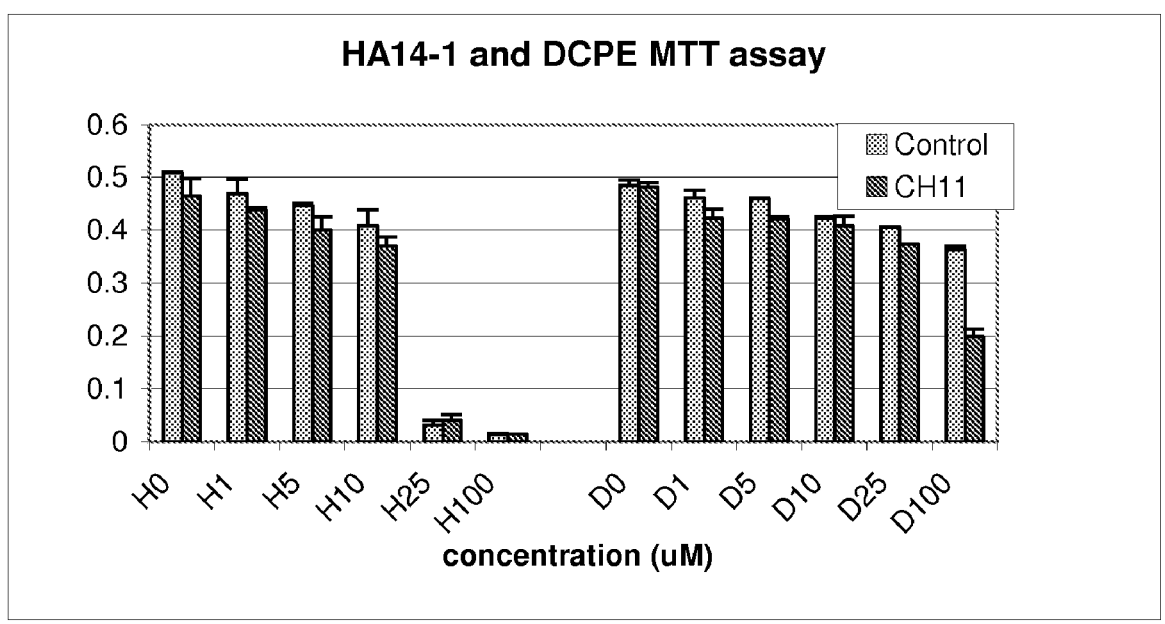
FIG. 4: depicts HA14-1 and DCPE in an MTT Assay for apoptosis sensitivity.

Two other putative Bcl family inhibitors are HA14-1 and 2,3 DCPE. HA14-1 is thought to be a Bcl-2 ligand [7], and 2,3-DCPE is thought to reduce the expression of Bcl-Xl and induce apoptosis in tumor cell lines [8]. As shown in FIG. 4, HA14-1 did not demonstrate any ability to sensitize cell to apoptosis, though at concentrations of 25-100 µM, HA14-1 had a fas-independent death-inducing effect on lesion cells. DCPE demonstrated a significant fas-dependent sensitization to apoptosis, but only at the highest tested dose of 100 µM.

FIG. 4 depicts the effect of HA14-1 and 2,3-DCPE on sensitivity to fas-induced apoptosis. Human lesion cells were plated and treated as above for 24 hours with the specified concentrations (1M) of HA14-1 (H) or 2,3-DCPE (D). Fas ligation was initiated with 50 ng/ml of activating antibody CH11 and 24 hours later the number of cell surviving was measured by their metabolism of MTT. Bars are mean±s.d. (n=2 per group). A reduction in MTT levels indicates cell death.

What is claimed is:

1. A method of treating restenosis and in-stent restenosis in a patient having a balloon catheter dilation procedure, comprising the step of (i) locally delivering a small molecule inhibitor of a Bcl protein directly to a balloon catheter dilation site within the patient, wherein said small molecule inhibitor of a Bcl protein is locally delivered by a balloon catheter, wherein the small molecule inhibitor of a Bcl protein does not cause general mitochondrial toxicity by inhibiting mitochondrial electron transport.

2. The method of claim 1, wherein the small molecule inhibitor of a Bcl protein is incorporated into a polymeric coating of a drug eluting stent.

3. The method of claim 1, wherein the small molecule inhibitor of a Bcl protein is selected from at least one member of the group consisting of: 2-methoxyantimycin $A_3$ and its analogs; 2,9-dimethoxy-11,12-dihydrodibenzo[c,g][1,2]-diazocine 5,6-dioxide (A); 5,5'-Dimethoxy-2,2'-dinitrosobenzyl (B); 2,[[3-(2,3-dichlorophenoxy)propyl]amino]ethanol-HCl; 2,2'-bis(8-Formyl-1,6,7-trihydroxy-5-isopropyl-3-methylnaphthalene); and Ethyl-2-amino-6-bromo-4-(1-cyano-2-ethoxy-2-oxoethyl)-4H-chromene-3-carboxylate.

4. The method of claim 1, wherein the said small molecule inhibitor is conjugated to a polymer to slow its diffusion from the site of balloon catheter dilation.

5. The method of claim 2, wherein the polymer used for polymeric coating is selected from at least one member of the group consisting of: polyvinyl alcohol (PVA), polytetrafluoroethylene (PTFE), phosphorylcholine, cationically modified phosphorylcholine polymer, poly(vinyl alcohol)-graft-poly (lactide-co-glycolide), polyethylene terephthlate, aliphatic polyester, acrylate-based polymers, carbon nanoparticles, collagen, 2-chloroparacyclophan, poly(2-chloroparaxylylene) layer modified by treatment with a sulfur dioxide plasma, polyurethane, PTFEP (poly(bis(trifluoroethoxy) phosphazene), polylactide, fluorinated polyphosphazenes and polymethacrylates, carbon film, hyaluronan, heparin-polycaprolactone-L-lactide, denatured collagen-polylactic-polyglycolic acid, poly-L-lactic acid, gelatinous photogel, and silicon carbide.

6. The method of claim 1, wherein the balloon catheter dilation procedure is angioplasty.

7. The method of claim 1, wherein the small molecule inhibitor of a Bcl protein is incorporated into a semi-permeable polymer membrane for direct local delivery of the small molecule inhibitor of the Bcl protein at the balloon catheter dilation site.

8. The method of claim 7, wherein the polymer used for polymeric coating is selected from at least one member of the group consisting of: polyvinyl alcohol (PVA), polytetrafluoroethylene (PTFE), phosphorylcholine, cationically modified phosphorylcholine polymer, poly(vinyl alcohol)-graft-poly(lactide-co-glycolide), polyethylene terephthlate, aliphatic polyester, acrylate-based polymers, carbon nanoparticles, collagen, 2-chloroparacyclophan, poly(2-chloroparaxylylene) layer modified by treatment with a sulfur dioxide plasma, polyurethane, PTFEP (poly(bis(trifluoroethoxy)phosphazene), polylactide, fluorinated polyphosphazenes and polymethacrylates, carbon film, hyaluronan, heparin-polycaprolactone-L-lactide, denatured collagen-polylactic-polyglycolic acid, poly-L-lactic acid, gelatinous photogel, and silicon carbide.

9. The method of claim 6, wherein the angioplasty is performed on a vessel selected from at least one member of the group consisting of: a coronary artery, a carotid artery, a renal artery, an iliac artery, a femoral artery, a peripheral artery, an anastomotic junction of a peripheral vein, and an internal mammary artery.

10. The method of claim 1, where the balloon catheter dilation is performed on a body lumen selected from at least one member of the group consisting of: a ureter, a lumen associated with the bladder, a lumen associated with the prostate, a urethra, a Fallopian tube, and a spinal outflow tract.

* * * * *